United States Patent [19]

Blake, III

[11] Patent Number: 5,045,077
[45] Date of Patent: Sep. 3, 1991

[54] BODY CAVITY DRAINAGE IMPLEMENT

[76] Inventor: Joseph W. Blake, III, 88 Main St., New Canaan, Conn. 06840

[21] Appl. No.: 116,390

[22] Filed: Nov. 3, 1987

Related U.S. Application Data

[63] Continuation-in-part of Ser. No. 801,205, Nov. 25, 1985, abandoned.

[51] Int. Cl.$^5$ ............................................. A61M 1/00
[52] U.S. Cl. .................................... 604/321; 604/318; 604/317; 55/310; 137/205
[58] Field of Search ............... 604/317, 318, 319, 321; 55/310, 312, 313; 220/203; 137/205; 141/59

[56] References Cited

U.S. PATENT DOCUMENTS

| | | | |
|---|---|---|---|
| 1,656,124 | 1/1928 | Melotte | 137/205 X |
| 3,463,159 | 8/1969 | Heimlich | 604/321 X |
| 3,713,444 | 1/1973 | Bridgman | 604/320 |
| 3,773,211 | 11/1973 | Bridgman | 604/319 X |
| 3,833,000 | 9/1974 | Bridgman | 604/319 X |
| 4,013,076 | 3/1977 | Puderbaugh et al. | 604/320 |
| 4,468,226 | 8/1984 | Kurtz et al. | 604/321 |
| 4,619,647 | 10/1986 | Kurtz et al. | 604/319 X |
| 4,650,497 | 3/1987 | Johnson | 604/321 |
| 4,664,660 | 5/1987 | Goldberg et al. | 604/321 |
| 4,738,671 | 4/1988 | Elliott et al. | 604/321 X |

FOREIGN PATENT DOCUMENTS

| | | | |
|---|---|---|---|
| 306324 | 3/1933 | Italy | 55/420 |
| 2051250 | 1/1981 | United Kingdom | 604/319 |

Primary Examiner—Carl D. Price
Attorney, Agent, or Firm—Seymour G. Bekelnitzky

[57] ABSTRACT

An article useful in the suction-assisted removal of fluids, including gases, such as air, and liquids, such as blood, from a body cavity which will prevent flow of gases therethrough into said cavity without the intervention of any liquid seals, in the event the pressure within said cavity becomes negative relative to the pressure at the discharge end of said article comprising a cap assembly, for fluid connection to said cavity and an accumulation chamber, for applying a controlled suction to said cavity, said assembly comprising a horizontal wall comprising at its periphery and normal thereto an annular wall for attachment to a liquid collection container surrounding said accumulation chamber; inlet means in fluid connection with said cavity, and, as desired, a liquid accumulation chamber or the atmosphere, through which said fluids may pass when the pressure within the cavity is greater than at the discharge end of said means; first one-way valve means associated with the discharge end of said inlet means for passing of said fluids from said cavity when the pressure in said cavity is positive relative to the pressure at the discharge end of said valve and which is closed when said cavity pressure is negative relative to the pressure at the discharge end of the valve to prevent flow of gases through said assembly into said cavity and negative pressure indicating means for measuring negative pressure in said cavity when said one-way valve means operates to seal its associated inlet means.

26 Claims, 5 Drawing Sheets

BODY CAVITY DRAINAGE IMPLEMENT

This application is a continuation-in-part of my co-pending application Ser. No. 801,205 filed on Nov. 25, 1985 now abandoned.

BACKGROUND OF THE INVENTION

This invention relates to an article useful in connection with the suction-assisted drainage of fluids, including gases, such as air, and liquids, such as blood, from a body cavity. More particularly, it relates to an article comprising inlet means to pass fluids therethrough to a liquid collection container from said body cavity, one-way valve means attached to the end of said inlet means to pass such fluids to said container when open and prevent the flow of gases therethrough, to the body cavity, when the valve is closed due to the pressure within the cavity being less than at the discharge end of said valve.

Violations of body cavities may occur for any of a number of reasons such as surgery, wounds or, in the case of pleural space invasion, rupture caused by coughing or disease. As a consequence atmospheric air, body gases and other fluids may invade the cavities and, e.g., in the case of pleurae, fill the pleural spaces thereby decreasing the lung capacity. If sufficient fluids accumulate the intimate contact between pleura and lung would be broken thereby preventing the outward pull of the pleura on the lung which results in shrinkage of the lung, i.e., a "collapsed" lung.

Another possible deleterious consequence of such a pleural space invasion would be a mediastinal shift in which the mediastinum, or space between the lungs, which contains such organs as the heart, is displaced from the center thereby compressing said organs. This could result in blood circulation problems and heart cessation.

Thus, it is desirable to remove such invasive fluids from the body cavities as quickly and completely as possible.

A typical prior art system for the collection of drained fluids from a body cavity includes three chambers connected in series. (Throughout this application a body cavity will be illustrated by pleural space and both terms will be used interchangeably.) They are first, a drainage collection chamber; second, a water seal chamber and third, a suction control chamber. The collection chamber accumulates any liquids drained from the body cavity. An air line passes from said chamber to the water seal chamber wherein the downstream end of said air line is positioned below the water level. The water seal chamber serves to maintain the vacuum pressure in the body cavity by preventing gases from passing upstream through the collection chamber to the body cavity, in the event the pressure therein decreases relative to the downstream pressure, thereby contaminating the body cavity. The water seal chamber is kept under vacuum. Because suction is maintained on the collection chamber air can reflux therethrough to the body cavity unless water (or another liquid) intervenes to prevent it. The depth of the end of the air tube below the water level in the water seal chamber controls the vacuum pressure at which the body cavity is drained. During the expiration of the patient, air drawn from the pleural cavity will pass to the water seal chamber where bubbling in the water seal will occur. The third, or suction control, chamber also provides water intervention above which the vacuum is maintained by direct connection to a vacuum source, generally a vacuum pump. The water intervention therein is directly connected to the atmosphere. While suction is being applied air will be drawn from either the connection to the atmosphere or the water seal chamber, i.e., from the source of least resistance. As long as the air moves from the atmospheric connection, the negative pressure in the pleural cavity will remainm constant. The pressure therein is controlled by the level of liquid in the suction control chamber.

The system described above, is typical of what will be referred to hereinafter as a "wet" drainage system. I.e., a system dependent upon liquid seals and the heights thereof for maintenance of vacuum in the pleural cavity and to prevent backflow of gases to the body cavity.

Such an apparatus is marketed by the Deknatel division of Howmedica, Inc. under the trademark PLEUR-EVAC.

A similar system which adds an additional suction control chamber, to allow the user to set both minimum and maximum vacuum levels within the body cavity is the THORA-TROL TM sold by Snyder Laboratories, Inc. of Dover, Ohio. This added feature permits the maintenance of vacuum despite incidents of negative pressure caused by coughing, for example, whereby the lung tissue is protected from sudden suction induced trauma.

Many other "wet" drainage systems have been described all of which are of interest but are not relevant in connection with the instant invention.

For instance, U.S. Pat. No. 4,540,413, to Russo, describes a system which will permit the drained fluids to be removed from the drainage chamber without disconnecting the unit from the patient. However, this unit depends upon a liquid seal in the rainage chamber to prevent entry of atmospheric air to the body cavity. Such a system suffers from the major drawbacks of the above devices, that is that an instantaneous decrease of pressure within the body cavity, e.g., due to gasping respiration of the patient could result in aspiration of the fluids within said chamber, including additives thereto such as anti-clotting agents, back into the body cavity or the increasing level of liquid in the chamber might progressively resist the drainage.

Furthermore, such a decrease in body cavity vacuum could result in reflux of the exuded gases thereinto before there is any, or much of a, liquid seal if such a seal depends upon the liquid draining from the cavity.

In addition, any debris present in the draining liquid might build up in or about the drainage tube thereby partially or completely clogging it. This could result in slower, or complete cessation of, drainage with the concomitant deleterious effects of poor drainage and/or excess pressure buildup in the body cavity.

All of the above systems suffer from the disadvantage of being cumbersome and position dependent in that any changes in the height of the liquid seals in the suction and/or water seal chambers thereof will affect the pressure applied to the body cavity.

Thus, in the prior art systems utilizing liquid seals to prevent backflow into the body cavity positioning of the unit in other than the customary vertical position, e.g., by upsetting thereof, could cause loss of such seals with increased vulnerability of the patient to pneumothorax. Such could not occur in the case of the instant invention which will close when the body cavity pressure is negative, relative to the vacuum chamber, regardless of the positioning of the unit.

In addition changes in water level as a result of, e.g., evaporation or entrainment in the evacuated gases might also affect accurate control of pressures within the system. To overcome those problems constant monitoring of, or periodic additions of water to maintain, the liquid levels of the water seal containing chambers is required with their concomitant cost in personnel time and potential for operator errors.

To avoid the above problems Heimlich, in U.S. Pat. No. 3,463,159 describes a one-way valve means to be attached to the discharge end of the inlet means which will prevent flow of gases therethrough to the body cavity when the pressure therein becomes less than that at the discharge end of the valve.

However, said device does not suggest nor teach the use of negative pressure indicating means to monitor the staus of the vacuum within the body cavity nor means for equilibrating said cavity with the environment at the discharge end of the one-way valve means.

Furthermore, in order to monitor functioning of the drainage system Heimlich also interposes a water seal between the body cavity and the vacuum source. Such an interposition will, of course, suffer from the limitations discussed above.

Throughout this specification the term 'dry' as used in connection with the present invention refers to the fact that no liquid seals are required for any reason, e.g., to prevent backflow of gases or control negative pressure in the body cavity. It does not imply that no liquids are present in the drainage chamber.

The present invention overcomes the above disadvantages by providing a cap assembly, for a liquid collection container, said cap assembly being removable from the container to render the patient ambulatory, comprising one-way valve means, to operate without intervention of liquid seals and independent of position, to prevent backflow of gases into the body cavity when the pressure therein becomes less than that of the environment, and negative pressure indicating means to permit monitoring of the condition of the patient even when the inlet means are closed by the one-way valve means, e.g., when the patient is ambulatory. If desired, the cap assembly will further comprise negative pressure relief means to permit entrance of gases to the body cavity to equilibrate same with the environment at the discharge end of the one-way valve means.

SUMMARY OF THE INVENTION

Accordingly, it is an object of the present invention to provide an inexpensive implement useful in the suction-assisted drainage of fluids, including gases, such as air and liquids, such as blood from a body cavity comprising one-way valve means to prevent the flow of gases, therethrough, into said cavity when the pressure therein becomes less than that of its environment and indicating means to monitor the pressure within said cavity.

It is another object of the invention to provide an implement, as described above, further comprising negative pressure relief means in fluid connection with said one-way valve means and negative pressure indicating means to permit entrance of gases to said body cavity to equilibrate same with the environment.

Yet another object of the invention is to provide an implement, as described above, comprising outlet means, for fluid connection with a vacuum source at its discharge end and the accumulation chamber at its inlet end, for passing gases from said said cavity through said chamber to said vacuum source.

Another object of the invention is to provide an implement, as described above, comprising regulator or adjustable valve means for maintaining a specified vacuum pressure at the inlet end of said outlet means.

Still another object of the invention is to provide an implement, as described above, comprising means disposed between the outlet means and accumulation chamber to prevent liquids from entering said outlet means, if said chamber overflows and/or contaminated gases from entering said chamber in the event of a cessation of the suction.

According to another object of the invention there is provided an implement, as described above, comprising positive pressure relief valve means for passing gases to the atmosphere when the pressure within the container becomes positive relative to the atmospheric pressure.

Yet another object of the invention is to provide an implement, as described above, comprising filter means for removing undesirable materials from the drained fluids received through the inlet stem and first one-way valve means of the cap assembly and passing the thusly purified fluids into said accumulation chamber said filter means surrounding said one-way valve and the discharge end of said inlet means.

Still another object of the invention is to provide an implement, as described above, comprising flow meter means associated with said outlet means for measuring the rate of gas flow through said means to the vacuum source.

Another object of the invention is to provide a system for use in the suction-assisted removal of fluids, including gases, such as air, and liquids, such as blood, from a body cavity by applying suction thereto, comprising: a cap assembly, for fluid connection to said cavity and, if desired, an accumulation chamber, for applying a controlled suction to said cavity, said assembly comprising a horizontal wall comprising: at its periphery, and normal thereto, an annular wall for attachment to a liquid collection container surrounding said accumulation chamber, inlet means in fluid connection with said cavity, and said liquid accumulation chamber, through which said fluids may pass when the pressure within the cavity is greater than at the discharge end of said means, first one-way valve means associated with the discharge end of said inlet means for passing of said fluids from said cavity when the pressure in said cavity is positive relative to the pressure at the discharge end of said valve and which is closed when said cavity pressure is negative relative to the pressure at the discharge end of the valve to prevent flow of gases through said assembly into said cavity, and negative pressure indicating means for measuring negative pressure in said cavity when said first one-way valve means operates to seal its associated inlet means; outlet means for passing gases from said chamber to a vacuum source, whereby a vacuum is created in said chamber; regulator or adjustable valve means for maintaining a specified vacuum pressure in said chamber by permitting atmospheric air to enter if the chamber pressure is less than said amount; pressure relief valve means for releasing gases from said chamber when said chamber pressure becomes positive relative the atmospheric pressure, filter means, surrounding the discharge end of the first one-way valve means for removing undesirable materials from the drained fluids received through said inlet stem and first one-way valve means and passing the thusly purified fluids into said accumulation chamber; flow meter means associated with said outlet means for measuring the rate of gas flow from the accumulation chamber to the vacuum source; negative pressure relief means in fluid connection with said inlet means and said negative pressure indicating means to permit entrance of gases into said body cavity to equalize the pressure within the cavity and the environment at the discharge end of the one-way valve, filter means disposed between said negative pressure relief means and said body cavity to remove contaminants from the entering gases; a housing comprising a wall surrounding a fluid accumulation chamber a large opening at its upper end to removably receive said cap assembly, and, if desired, at least one closable opening at the opposite lower end, for periodic or continuous removal of fluids entering or accumulating in said chamber, and, if desired, at least one self-sealing opening in at least one sidewall, of said housing, for removal of samples therefrom or addition of materials thereto; and means, disposed between said outlet means and said chamber, to prevent the drained fluids from entering the outlet means if the chamber overflows and/or contaminated gases from entering the chamber if atmospheric air is permitted to enter through the vacuum pressure regulator.

According to another object of the invention there is provided a drainage system, as described above, wherein said means to prevent overflowing liquids from entering the outlet means and/or contaminated air from entering the chamber comprises a filter assembly comprising a filter mounting disc, for filter means, said disc comprising: an outer horizontal wall comprising a first inlet stem through which the outlet end of the inlet stem of the cap assembly with its associated one-way valve means may pass, an inner horizontal wall to which the filter means may be removably affixed; and means for effecting a vacuum-tight sealing of the space between said inlet stems said inner and outer walls being vertically spaced from each other, and a hydrophobic filter disc lying upon said upper side of said mounting disc, said filter disc comprising a hole therethrough which is concentric, and whose edges are in sealing contact, with the outer wall of the inlet stem of said mounting disc.

Yet another object of the invention is to provide a system which is a simple, easily fabricated unit comprising a minimal number of chambers wherein all or most of the control and indicating means are not of the liquid type and are contained in the cap assembly.

Other embodiments or modifications may be suggested to those having the benefit of the teachings herein and are a part of the invention to the extent they fall within the scope and spirit of the subjoined claims.

DETAILED DESCRIPTION OF THE PREFERRED EMBODIMENTS

Reference is now made specifically to the drawings in which identical or similar parts are designated by the same reference numbers throughout.

Figure 1:
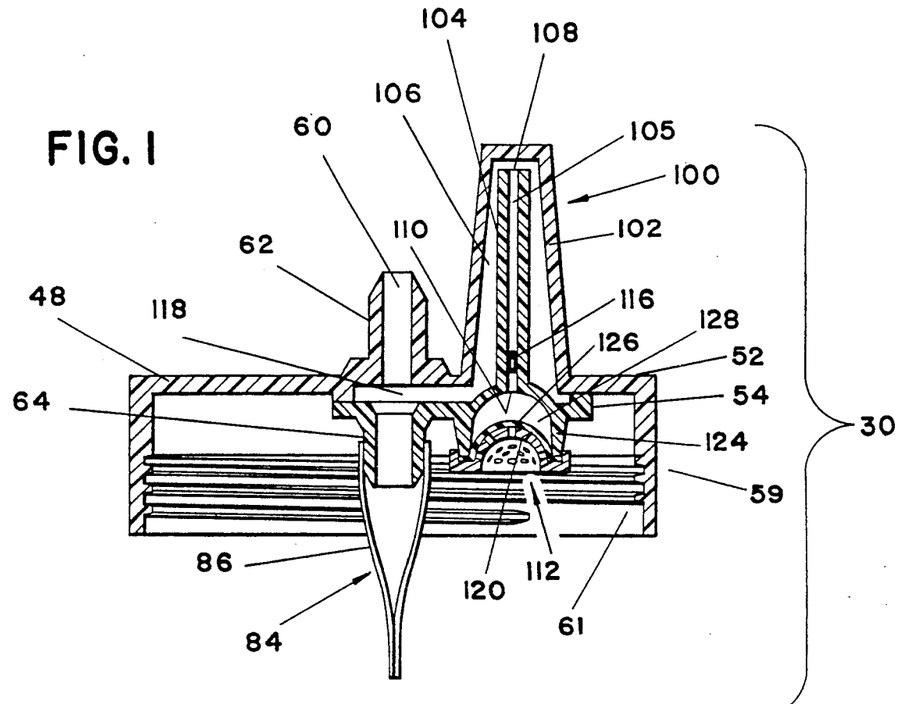
FIG. 1 is a front elevational sectional of one embodiment of the instant invention.

FIG. 1 illustrates a cap assembly 30 for attachment to a housing surrounding a chamber to accumulate fluids drained from a body cavity (not shown) with the assistance of suction.

The drainage system comprising said cap assembly and chamber has the advantage over prior art systems that the cap assembly may be removed from the chamber, in order to render the patient ambulatory, and to prevent the flow of gases from the environment into the body cavity while monitoring the negative pressure within said cavity.

Said cap assembly 30 comprises a flat, horizontal top wall 48 comprising threads 61 around a circular vertical wall 59 so that said cap may be removably and sealably attached to the upper wall of said housing. It is, of course, to be understood that means, other than threads, may be used to secure the cap assembly to the housing.

The cap assembly as normally used is in fluid connection with the patient through inlet means comprising an inlet opening 60 and upward and downward projecting stems 62 and 64, respectively, said opening and stemps being coextensive with inlet opening 60 therethrough.

One-way valve means, preferably a sleeve valve such as duckbill valve 84 is connected to the end of stem 64 which is opened to pass the body fluids when the pressure within the cavity is greater than that at the discharge end of the valve and closes to prevent backflow of said gasses when said pressures are reversed.

The sleeve portion 86 of said valve is elongated and soft enough to be capable of closing itself up- and downstream of a non-fluid mass moving from the body cavity through said valve when it is necessary for the valve to be closed.

Thus, it would not be possible for gasses to flow into the body cavity through valve 84 when the pressure in the body cavity is less than at the drainage end of said valve even when a nonfluid mass is present in the sleeve portion 86 thereof.

A negative pressure indicating device 100 is positioned adjacent to inlet opening 60. Device 100 includes an upright sealing cover 102 made of a transparent material having a base connected to outer portion 54 of, and a top wall spaced from, top wall 48. An elongated upright indicating tube 104 is positioned within cover 102; tube 104 and cover 102 form an elongated circular hollow 106. Tube 104 forms a vertical channel 105 having opposed top and bottom openings 108 and 110, respectively. Top top opening 108 is in fluid connection with hollow 106.

Bottom opening 110 opens at outer portion 54 of top wall 48 but is blocked from fluid connection with the environment by a pressure transmission device 112 that is connected to said outer portion 54 and positioned between bottom opening 110 and the environment. Tube 104 has an outer surface having markings 114 with associated indicia indicating negative pressure in the body cavity relative to the pressure of the environment external thereto. An indicator pellet 116 positioned in vertical channel 105 is movable between upper and lower positions along markings 114. A passage 118 is formed by top wall 48 between circular hollow 106 and inlet opening 60. Pressure transmission device 112 includes an upwardly oriented retaining dome member 120, which comprises slots 122 adapted to pass gases from the environment. Dome member 120 has a rim affixed to a downwardly extending flange 124 connected to outer portion 54 of top wall 48. An elastic diaphragm 126 is attached to the rim of dome member 120 and to flange 124. Indicator pellet 116, indicating tube 104, and elastic diaphragm 126 define a plenum chamber 128. Elastic diaphragm 126 expands upwardly away from dome member 120 when gases on its outer side pass through slots 122 so as to cause indicator pellet 116 to move upwardly in indicating tube 104 along markings 114.

In addition, if desired, the cap assembly may also comprise filter means (not shown) for removing undesirable materials from the drained fluids received through the inlet stem and first one-way valve means of the cap assembly and passing the thusly purified fluids into said accumulation chamber said filter means surrounding said one-way valve.

Figure 2:
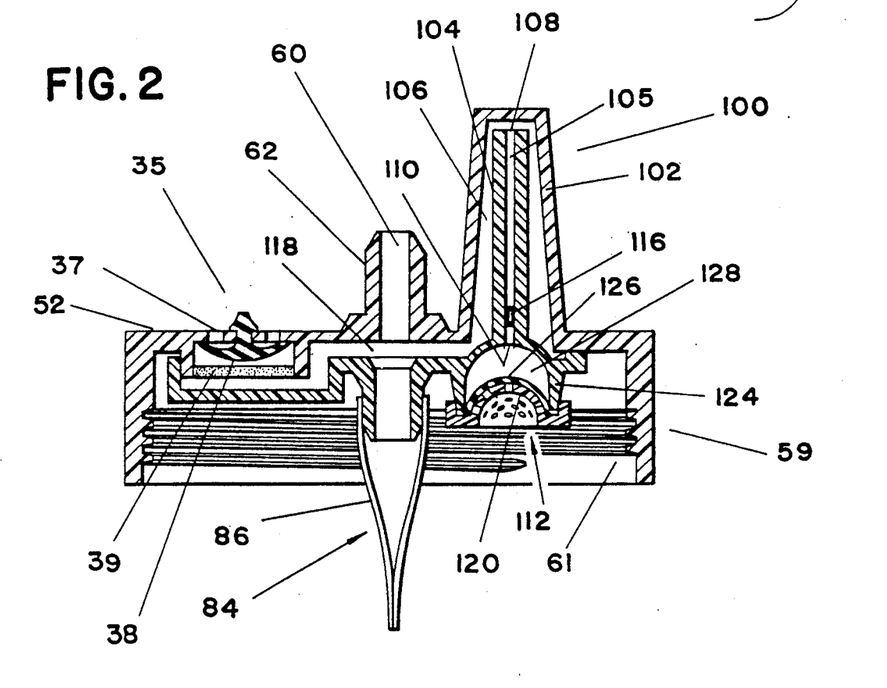
FIG. 2 is a front elevational sectional of another embodiment of the invention.

If desired, as shown in FIG. 2, the cap assembly also comprises negative pressure relief means 35, in fluid connection with inlet opening 60 and negative pressure indicating device 100, to permit entrance of gases into the body cavity, after one-way valve 84 has closed, in order to equilibrate the pressure within said cavity with the environment. Said relief means 35 mounted in the top portion 52 of top wall 48. Crown portion 38 thereof is adapted to be opened by atmospheric air, when the pressure within the body cavity is less than that of the environment, by means of air passing through a ring of holes 37 formed in the top wall. Said relief further comprises filter means 39 positioned within said wall and disposed between said relief means 35, said inlet opening 60 and said indicating device 100 to remove contaminants from the air entering the body cavity.

It is, of course, to be understood here, as well as in other parts of the specification, that references to umbrella relief valves include other devices, known to the art, including spring loaded valves.

Figure 3:
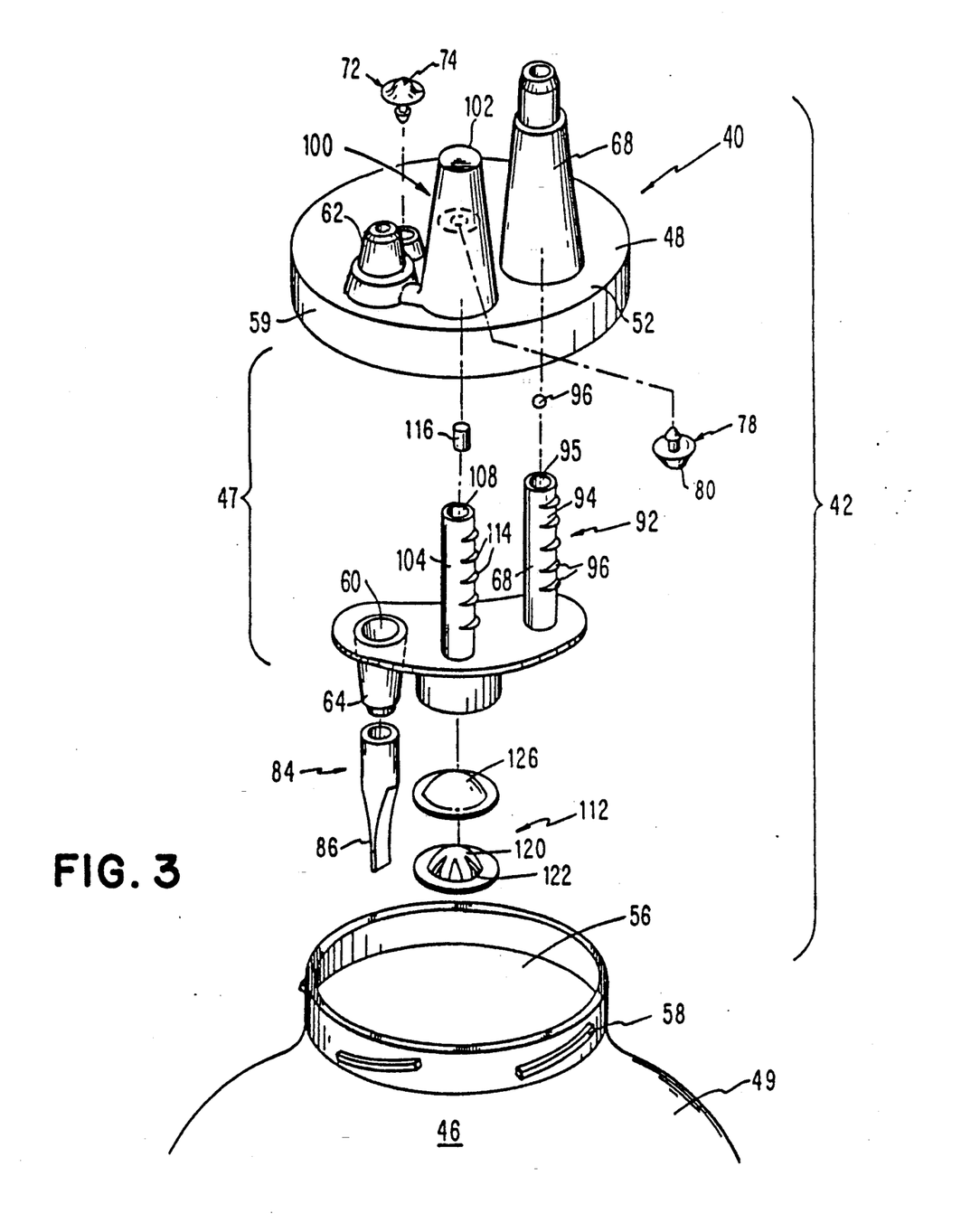
FIG. 3 is an exploded partial perspective view of another embodiment.
Figure 4:
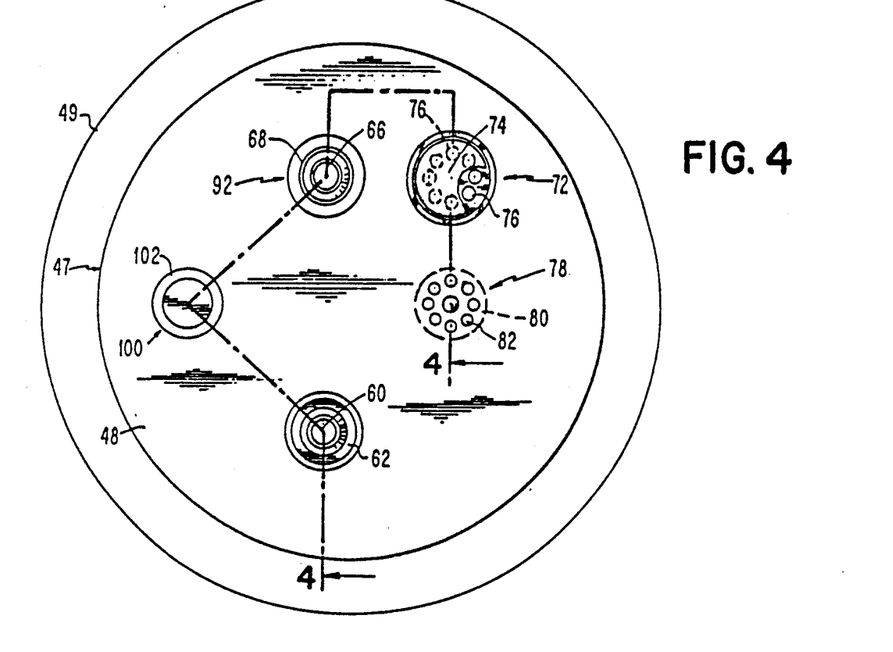
FIG. 4 is a top view of the above embodiment.
Figure 5:
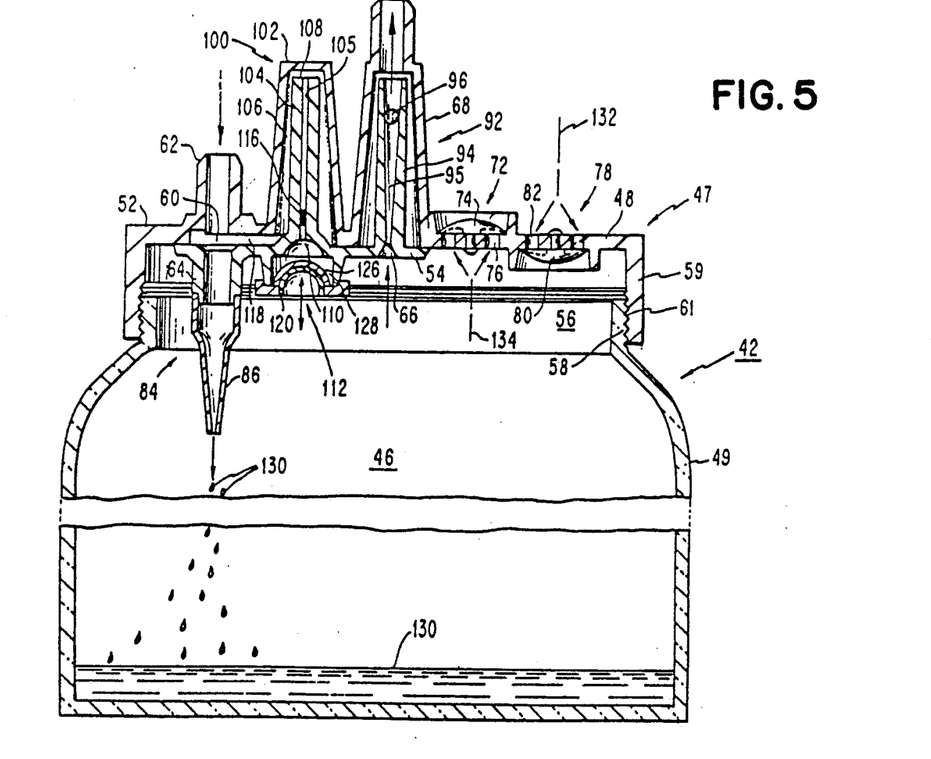
FIG. 5 is a sectional side view along line 4—4 of FIG. 4.

In another embodiment of the invention, as shown in FIGS. 3 to 5 the cap assembly will also comprise positive pressure relief means 72 mounted at the upper side of top wall 48 with its crown portion 74 positioned so as to be opened by gases within a vacuum chamber, when present, through a ring of holes 76 formed within said wall and proximal to said chamber, when the pressure therein becomes greater than the atmospheric air pressure.

In yet another aspect of the invention the cap assembly comprises negative pressure relief means, such as a pre-set, suction-control valve as exemplified by umbrella valve 78 mounted to the upper side of top wall 48. The crown portion 80 of umbrella valve 78 is positioned and adapted to be opened by the pressure of atmospheric air through a ring of holes 82 formed in top wall 48 when the differential between the pressure in the vacuum chamber and the atmospheric pressure becomes greater than a predetermined value for umbrella valve 78.

In another aspect of the above embodiment the cap assembly comprises an outlet opening 66 in top wall 48 for gas connection to the vacuum chamber 46, when present, and a source of suction, such as a vacuum pump (not shown). An upwardly extending nipple 68 connected to said wall is coextensive with outlet opening 66.

An air metering device 92 is positioned at the outlet opening 66. Device 92 includes an elongated upright metering tube 94 positioned within nipple 68 and having a base connected to the upper portion of top wall 48 and an outlet end spaced below the outlet of nipple 68. An upwardly flared vertical channel 95 is formed within metering tube 94. A flow indicator pellet 96 is positioned within channel 95. Pellet 96 rises and falls in metering tube 94 in accordance with the rate of gas flow from vacuum chamber 46 to the suction source. The taper of channel 95 increases in diameter with height. Flow rate markings 98 with associated indicia are positioned on the outer surface of metering tube 94. Markings 98 can be viewed through nipple 68, which is made of a transparent material. Indicator pellet 96 is movable vertically between lower and upper positions along markings 98 in accordance with the gas flow, with indicator pellet 96 resting upon the taper of channel 95 at the lower position.

In the practice of using the cap assembly of the invention in conjuction with a vacuum chamber, as illustrated in FIGS. 3–5, a suction source (not shown) applies suction, through the outlet opening 66, upon the body cavity through chamber 46.

When the patient inhales, a positive pressure is created in the body cavity relative to the pressure in vacuum chamber 46 causing body fluids, including gases such as air, and liquids such as blood, to pass through inlet opening 60 and valve 84 to vacuum chamber 46 where the liquids accumulate in the chamber and the gases are sucked out. When the pressure in vacuum chamber 46 drops below a predetermined value, regulator valve 78 opens by pressure of atmospheric air to allow entry of said air until the vacuum chamber pressure is raised to said value. The path of the incoming atmospheric air through said regulator valve 78 is shown by phantom arrowed lines 132. In the event the pressure in vacuum chamber 46 rises above the atmospheric pressure, relief means 72 will open to vent the excess pressure to the atmosphere. Such an event can occur when the exhale of the patient is strong enough to create positive pressure in chamber 46 relative to the atmosphere. This flow of gases is shown in FIG. 5 by phantom arrowed lines 134. After the patient exhales, a negative pressure will be created in the pleural cavity relative to that in the vacuum chamber which will cause sleeve portion 86 of valve 84 to close thereby preventing the backflow of gases from the chamber to the cavity. At about the same time elastic diaphragm 126 of the pressure transmission device 112 is raised as the pressure at the upper side of indicator pellet 116 is less than the pressure in vacuum chamber 46 with the result that pressure is transmitted through plenum chamber 128 to raise indicator pellet 116 along markings 114 whereby an operator can determine the negative pressure in the pleural cavity. Furthermore, when vacuum chamber 46 is being drained of gases through outlet 66 indicator pellet 96 is raised in metering tube 94 allowing the operator to determine the gas flow rate by means of markings 98.

Figure 6:
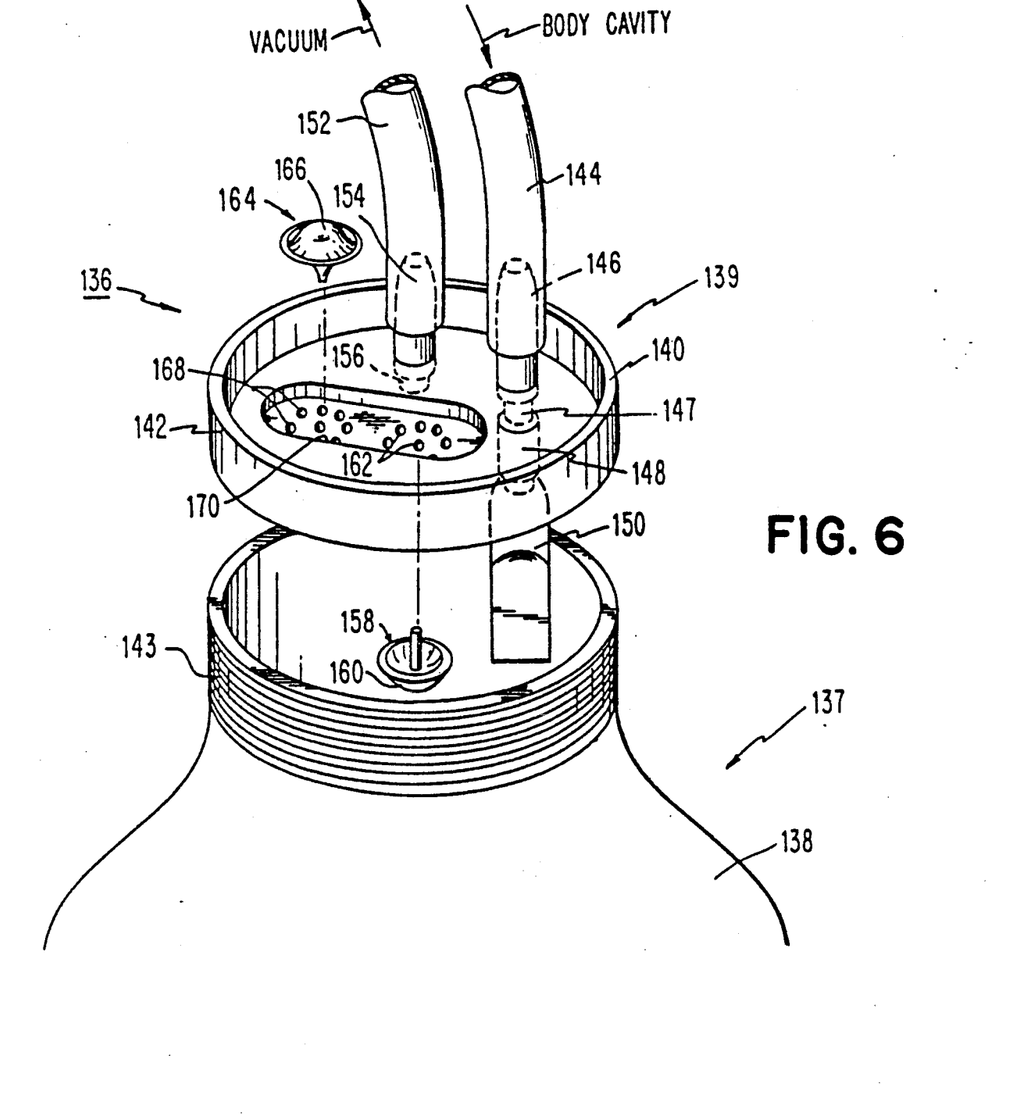
FIG. 6 is an exploded perspective view of a simplified embodiment of the invention.

A simplified embodiment 136 of the invention is illustrated in an exploded perspective view in FIG. 6. System 136 includes a container 137 forming a sealed vacuum chamber 138 having a cap assembly 139 which comprises a top wall 140 which also forms the top wall of vacuum chamber 138. Cap assembly 139 comprises a circular, downwardly depending flange 142 comprising internal threads to mate with the external threads 143 of the container. (It is, of course, to be understood that other means, as known to the art, for attaching the cap assembly to the container may be employed.) A flexible inlet tube 144 in fluid connection with the pleural cavity of the patient is removably attached to the nipple of an external connecting inlet tube 146 extending perpendicularly upward from and connected to top wall 140. An internal connecting inlet tube 148 fluidly coextensive with inlet tube 146 via inlet port 147 in top wall 140 is connected to and extends perpendicularly downward from top wall 140 into vacuum chamber 138. A one-way valve means sleeve valve, preferably an extended floppy duckbill valve 150, as shown, is removably attached to the outlet port of internal inlet tube 148. Valve 150 opens to pass fluids from the pleural cavity to vacuum chamber 138 when the pressure in the cavity is greater than in chamber 138. Valve 150 is elongated and is capable of closing about a non-fluid mass of material drained from said cavity thereby preventing the sleeve portion thereof from being forced open to permit backflow of gases to the cavity when the pressure therein is less than at the discharge end of the valve.

A flexible outlet tube 152 is removably attached to an external connecting outlet tube 154 extending perpendicularly upward from top wall 140. Outlet tube 154 is coextensive with outlet opening 156 formed in top wall 140. Outlet opening 156 is in fluid connection with vacuum chamber 138 and a vacuum source, or gravity.

A regulator valve 158, preferably an umbrella valve similar to valve 80 described in relation to FIG. 3, is mounted to the under side of top wall 140. The crown portion 160, which is positioned proximal to the vacuum chamber is adapted to be opened by the pressure of atmospheric air through a ring of holes 162 formed in top wall 140 when the differential between the atmospheric and chamber pressures exceeds the predetermined value for said valve.

A positive pressure relief valve 164, preferably an umbrella type, is mounted with its crown portion 166 at the outer side of top wall 140. Crown portion 166 is adapted to be opened by gases in the vacuum chamber 138 passing through a ring of holes 168, formed in top wall 140, when the vacuum chamber pressure exceeds that of the atmosphere.

The outer side of top wall 140 preferably has a depression 170 wherein the holes 162 and 168 are formed.

The operation of system 136 is as described above for system 10.

Figure 7:
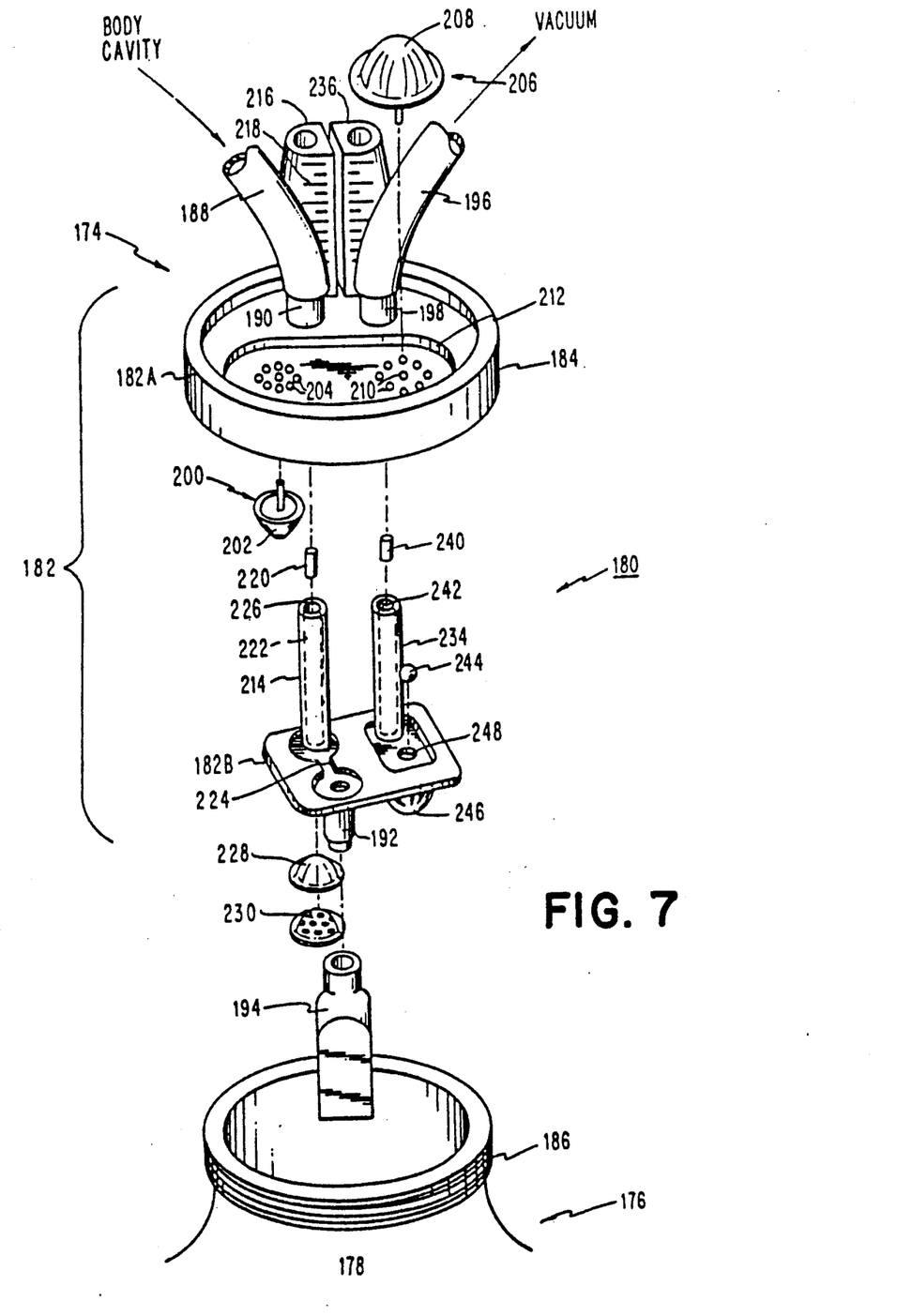
FIG. 7 is an exploded perspective view of another embodiment of the invention.

Another embodiment of the invention, designated as system 174, is shown in FIG. 7. This system comprises a container 176, forming a sealed vacuum chamber 178 comprising a cap assembly 180 which includes a top wall 182 that forms the top wall of vacuum chamber 178. Top wall 182 is shown in FIG. 7 as including an outer portion 182A connected to an inner portion 182B, but the two portions can be considered a unitary wall. Cap assembly 180 comprises a circular, downwardly depending flange 184 for attachment to the container by known means. A flexible inlet tube 188 in fluid connection with the pleural cavity of the patient is removably attached to the nipple of an external connecting inlet tube 190 extending perpendicularly upward from and connected to top wall 182.

An internal connecting inlet tube 192 coextensive with external inlet tube 190 extends perpendicularly downward into the vacuum chamber 178 from the underside of top wall 182. A one-way valve means, preferably a floppy duckbill valve 194, as shown, is removably attached to the discharge end of internal inlet tube 192. Valve 194 has the same function as valves 84 and 150 of systems 10 and 136, respectively, as discussed above.

A flexible outlet tube 196 is removably attached to an external connecting outlet tube 198 extending perpendicularly upward from top wall 182. Outlet tube 198 is coextensive with the outlet opening formed in top wall 182.

A regulator valve 200, preferably an umbrella valve similar to valve 80 described in relation of FIG. 3, is mounted to the under side of top wall 182. The crown portion 202, which is positioned proximal to the vacuum chamber is adapted to be opened by the pressure of atmospheric air through a ring of holes 204 formed in top wall 182 when the differential between the atmospheric and chamber pressures exceeds the predetermined value for said valve.

A positive pressure relief valve 206, preferably an umbrella type, is mounted with its crown portion 208 at the outer side of top wall 182. Crown portion 208 is adapted to be opened by gases in the vacuum chamber 178 passing through a ring of holes 210, formed in top wall 140, when the vacuum chamber pressure exceeds that of the atmosphere.

The outer side of top wall 182, in particular upper portion 182A, preferably has a depression 212 wherein the holes 204 and 210 are formed.

A negative pressure indicator includes a pressure tube 214 extending vertically upward from top wall portion 182B, disposed within a transparent sealing cover 216 likewise extending upward from top wall 182 and having indicia 218 indicating pressure within vacuum chamber 178. Pressure indicator slug 220 is slidably positioned within channel 222 of pressure tube 214. A gas flow passage 224 between internal inlet tube 192 and a hollow (not shown in FIG. 7) is formed between sealing cover 216 and pressure tube 214 and the top opening 226 of channel 222. An elastic diaphragm 228, mounted around its edges to a dome member 230 and provided with gas passages is capable of rising or falling in accordance with the gas pressure differential between vacuum chamber 178 and the body cavity. The operation of diaphragm 228 and the negative pressure indicator is as described in connection with diaphragm 126 and FIG. 3. A gas flow indicator including a gas flow tube 234 extending perpendicularly upward from top wall 182 is disposed within a transparent sealing cover 236 likewise extending upwardly from top wall 182 and having indicia 238 indicating gas flow from vacuum chamber 178 to the suction source. Indicator slug 240 is slidably positioned within channel 242 of tube 234.

Pressure tube 214 along with sealing cover 216 and gas flow tube 234 with sealing cover 236 are spaced from the inlet and outlet tubes 190 and 198, respectively, and preferably adjoin each other in a single unit.

In another embodiment of the invention the cap assembly further comprises sealing means disposed between the outlet means and accumulation chamber to prevent liquids from entering said outlet means if said chamber overflows.

In one aspect of the above embodiment said sealing means consists of a liquid overflow ball-check valve for sealing off vacuum intake via tube 198 which includes a floating ball 244 that is ordinarily seated in a cage 246 having slots for passing either gasses or liquids. Cage 246 is secured to the underside of top wall 182. The top of cage 246 has an outlet port 248 having a diameter less than ball 244. The bottom of cage 246 is spaced far enough below outlet port 248 so that ball 244, when at the bottom of the cage, does not block outlet port 248. Ball 244 is adapted to float when liquids from the body cavity fill vacuum chamber 178 beyond the bottom of cage 246. When the liquid level within cage 246 rises to such a point ball 244 will float high enough to close outlet port 248, thus blocking off further suction and effectively ceasing the fluid flow from the body cavity.

In another aspect of the above embodiment the sealing means consists of a hydrophobic filter (not shown).

The vacuum pressure control valves, for use in the articles of the invention, may be of a fixed or adjustable value type. For purposes of economy a fixed value valve such as an umbrella valve is preferably used.

In using the above described embodiments of the invention the cap assembly may be removed from the vacuum chamber without fear of entrance of contaminated gases into the body cavity, and the negative pressure therein constantly monitored.

Furthermore, if desired, the pressures of the body cavity and environment may equilibrated at any time including those times when the patient is ambulatory and not attached to the collection device or vacuum source.

By virtue of some, or all, of the valves and controls being present in the cap assembly it is possible to manufacture a simple, inexpensive, essentially unitary device for draining fluids from a body cavity said device comprising only said cap assembly and a single collection chamber—a feat that was not possible with the prior art drainage devices.

It should also be appreciated that, as liquid seals are not required, nor will they serve any useful purpose, in the drainage systems of this invention these systems are not subject to problems caused by changes in the liquid heights as a consequence of changes in position from the essentially vertical, evaporation or entrainment of the sealing liquids in the evacuating gases or operator errors.

Furthermore, there are additional savings in that personnel are not required to take the time to "prime" the units with controlling liquids, measuring their heights and replacing liquids lost as a result of the above indicated evaporation or entrainment.

The embodiments of the invention particularly disclosed and described hereinabove are presented merely as examples of the invention. Other embodiments, forms and modifications of the invention coming within the proper scope and spirit of the appended claims will, of course, readily suggest themselves to those skilled in the art.

What is claimed is:

1. An article useful in the suction-assisted removal of fluids, including gases, such as air, and liquids, such as blood, from a body cavity which will prevent backflow of gases into said cavity, without the intervention of any liquid seals, in the event the pressure within said cavity becomes negative relative to the pressure at the discharge end of conduit means for passing said fluids from the body cavity to an accumulation chamber surrounded by a container for the collection of said liquids, wherein said article consists of a removable cap assembly, for said container, consisting of A. a hollow chamber within a housing comprising:
  i) a first horizontal wall, consisting of a flat member containing a first port therethrough, at one end;
  ii) a large opening at the end opposite said first horizontal wall; and
  iii) an annular wall descending from the periphery of said first horizontal wall to said large opening;

B. conduit means, for passing said fluids through the cap into the hollow chamber, said conduit means consisting of
  i) an inlet stem rising from the first port;
  ii) a vertical elongated tubular element, containing a port in its side wall, attached at one end to said said inlet stem at said first port in the first horizontal wall and terminated at its other end by a discharge stem; and
  iii) negative pressure transmission means to transmit changes in negative pressure to negative pressure indicating means;

C. one-way valve means, associated with the discharge stem of said conduit means, which will permit the flow of fluids therethrough when the pressure at the inlet stem is greater than that at the discharge stem of the valve and will close to prevent flow of fluids therethrough when the pressure at the inlet stem is less than that at said discharge end; and D. negative pressure detecting and indicating means, in negative pressure-indicating connection with said conduit means, through said negative pressure transmission means, for indicating the negative pressure in the body cavity, when said one-way valve means is closed consisting of:
  i) negative pressure indicating means rising from the outer surface of the first horizontal wall; and
  ii) means for connecting said negative pressure indicating means to the negative pressure transmission means of the conduit means.

2. The article according to claim 1, wherein said negative pressure indicator means includes a vertical tube having opposed top and bottom openings, said bottom opening being formed by said cap horizontal wall, said tube having an outer surface having markings indicating said negative pressure in said cavity; an indicator pellet positioned in and sealing said vertical tube movable between upper and lower positions along said markings; a transparent cover member connected to and extending upwardly from said the upper side of said cap, positioned around and spaced from said vertical tube, said vertical tube and said cover member forming an elongated circular hollow in fluid communication with said top opening of said vertical tube; a passage formed by the horizontal wall of said cap between said hollow and said inlet means; and pressure transmission means connected to said wall positioned between said bottom opening of said vertical tube and the external environment, said pressure transmission means transmitting negative differential pressure to said vertical tube upon closure of said first one-way valve means, wherein said indicator pellet is moved between said upper and lower positions in accordance with said negative pressure in said cavity.

3. The article according to claim 2, wherein said pressure transmission means includes an upwardly oriented retaining dome member forming slots adapted to pass gases, said dome member having a rim affixed to said cap wall below said lower opening of said vertical tube, a diaphragm covering said dome and affixed to said rim of said dome, said indicator pellet, said vertical tube, and said diaphragm defining a plenum chamber wherein gases are capable of passing through said slots and expanding said diaphragm upwardly so as to move said indicator pellet upwardly in said vertical tube in accordance with said negative pressure.

4. The article of claim 1 wherein said cap assembly further comprises negative pressure relief means in fluid connection with said inlet means and said negative pressure indicating means to permit entrance of gases into said body cavity to equalize the pressure within the cavity and the environment at the discharge end of the one-way valve.

5. The article of claim 4 wherein said cap assembly further comprises filter means disposed between said negative pressure relief means and said body cavity to remove contaminants from the entering gases.

6. The article of claim 5 wherein said filter means comprises a hydrophobic filter.

7. The article of claim 1 wherein said cap assembly further comprises outlet means which provides fluid connection between a vacuum source and the accumulation chamber.

8. The article of claim 7 wherein said cap assembly further comprises sealing means disposed between the outlet means and accumulation chamber to prevent liquids from entering said outlet means if said chamber overflows.

9. The article of claim 8 wherein said sealing means is a ball-check valve positioned at the underside of said cap wall at the intake end of said outlet means.

10. The article of claim 9 wherein said valve includes a cage member secured to said cap wall underside at the intake end of said outlet means, said cage member having a lower portion spaced from said top wall and forming apertures capable of passing a fluid, a ball member positioned in said cage ordinarily disposed at said cage lower portion below said outlet means, said outlet means comprising a port in said cap wall, said ball member having a diameter greater than that of the port, said ball member being adapted to float upwardly to block said outlet port when the liquid rises to overflow said vacuum chamber whereby liquids are prevented from being removed from said chamber and the flow of the liquid from said cavity into said chamber ceases.

11. The article of claim 7 further comprising flow meter means associated with said outlet means for measuring the rate of gas flow through said means to the vacuum source.

12. The article of claim 11 wherein said flow meter means includes a tapered tube positioned coextensively within said outlet means and a flow indicator pellet positioned within said tapered tube, said tapered tube being disposed vertically with the taper of said tube increasing in diameter with height, said tube having an outer surface having markings indicating rate of gas flow, said flow indicator pellet being movable along said markings between lower and upper positions in accordance with said flow said flow indicator pellet resting upon said taper of said tube at said lower position when the gas flow rate is less than a specified amount.

13. The article of claim 12 wherein said flow meter means includes a transparent nozzle extending upwardly from said upper side of said cap, said nozzle enclosing said tapered tube.

14. The article of claim 1 wherein said cap assembly further consists of negative pressure regulator means for maintaining a specified vacuum pressure within the accumulation chamber.

15. The article of claim 14 wherein wherein said regulator valve is an umbrella valve capable of opening to allow entrance of atmospheric air when the pressure thereof is greater than that in the accumulation chamber by more than a specified amount.

16. The article of claim 1 wherein said cap assembly further comprises positive pressure relief valve means for passing gases to the atmosphere when the pressure within the container becomes positive relative to the atmospheric pressure.

17. The article of claim 16 wherein said pressure relief valve means is an umbrella valve capable of opening to allow escape of gases from the accumulation chamber when the pressure therein is greater than the atmospheric air pressure.

18. The article of claim 1 wherein said first one-way valve is a duckbill valve having a sleeve portion long enough to close about a particle traveling therethrough and seal the fluid connection with the body cavity to prevent flow of gases thereto when said valve is closed.

19. The article of claim 1, wherein the annular vertical wall consisting of an upper and a lower portion, further consisting of an upper, closed second hollow chamber within said first hollow chamber defined by said first horizontal wall, the upper portion of said vertical wall and a second horizontal wall consisting of a flat member, containing a second port opposite the first port of the first horizontal wall, said member being attached to the vertical wall at the junction of its upper and lower portions; an open third hollow chamber within said first hollow chamber defined by said second horizontal wall, the lower portion of said vertical wall and the large opening;

wherein the vertical element of the conduit means passes through the ports in the horizontal walls, to pass the fluids through said second chamber, and comprises a third port for pressure detecting connection with the negative pressure detecting and indicating means in the portion of said vertical element within said second chamber.

20. The article of claim 1 further consisting of:
A. negative pressure relief means in fluid connection with said inlet means and said negative pressure indicating means to permit entrance of gases into said body cavity to equalize the pressure within the cavity and the environment at the discharge end of the one-way valve;
B. first outlet means, in fluid connection with a vacuum source at its discharge end and the accumulation chamber at its inlet end, for passing gases from said cavity through said chamber to said vacuum source;
C. negative pressure regulator valve means for maintaining a specified vacuum pressure within the accumulation chamber; and
D. positive pressure relief valve means for passing gases to the atmosphere when the pressure within the container becomes positive relative to the atmospheric pressure.

21. The article of claim 20 further consisting of filter means disposed between said negative pressure relief means and said body cavity to remove contaminants from the entering gases.

22. The article of claim 20 further consisting of flow meter means associated with said outlet means for measuring the rate of gas flow through said means to the vacuum source.

23. The article of claim 20 further consisting of barrier means disposed between the outlet means and the chamber to prevent liquids from entering said outlet means if said chamber overflows.

24. The article of claim 20 further consisting of:

A. filter means disposed between said negative pressure relief means and said body cavity to remove contaminants from the entering gases;

B. flow meter means associated with said outlet means for measuring the rate of gas flow through said means to the vacuum source; and C. barrier means disposed between the outlet means and the chamber to prevent liquids from entering said outlet means if said chamber overflows;

25. The article of claim 1 wherein said cap assembly further consists of means for removably attaching the cap assembly to the container.

26. The article of claim 25 wherein said attachment means consists of a threaded portion on the inner surface of said annular wall adjacent said large opening.

* * * * *